US010670551B2

(12) United States Patent
Fotopoulou et al.

(10) Patent No.: US 10,670,551 B2
(45) Date of Patent: Jun. 2, 2020

(54) SYSTEM AND METHOD FOR VOLTAGE MEASUREMENTS ON BIOLOGICAL TISSUES

(71) Applicant: Imperial College of Science, Technology and Medicine, London (GB)

(72) Inventors: Christina Fotopoulou, London (GB); Emmanuel Drakakis, London (GB); Hani Gabra, London (GB); Martyn Boutelle, London (GB)

(73) Assignee: Imperial College of Science, Technology and Medicine, London (GB)

( * ) Notice: Subject to any disclaimer, the term of this patent is extended or adjusted under 35 U.S.C. 154(b) by 70 days.

(21) Appl. No.: 15/754,396

(22) PCT Filed: Aug. 25, 2016

(86) PCT No.: PCT/GB2016/052639
§ 371 (c)(1),
(2) Date: Feb. 22, 2018

(87) PCT Pub. No.: WO2017/033018
PCT Pub. Date: Mar. 2, 2017

(65) Prior Publication Data
US 2018/0252666 A1    Sep. 6, 2018

(30) Foreign Application Priority Data

Aug. 25, 2015 (GB) .................... 1515115.2

(51) Int. Cl.
*A61B 5/05*       (2006.01)
*G01N 27/403*     (2006.01)
(Continued)

(52) U.S. Cl.
CPC ....... *G01N 27/4035* (2013.01); *A61B 5/0004* (2013.01); *A61B 5/04002* (2013.01);
(Continued)

(58) Field of Classification Search
CPC ........ A61B 5/05; A61B 5/053; G01N 27/327; G01N 27/403
See application file for complete search history.

(56) References Cited

U.S. PATENT DOCUMENTS 3,957,613 A      5/1976  Macur
4,407,300 A *   10/1983  Davis ...................... A61B 5/05
                                                      600/547
(Continued)

FOREIGN PATENT DOCUMENTS

EP    0650694    3/1995
JP    S563677    1/1981

OTHER PUBLICATIONS

Zeuthen, "Potentials and small-signal impedances of platinum microelectrodes in vivo and in vitro," Med. & Biol. Eng. & Comput., 1978, 16, 489-499 (Year: 1978).*
(Continued)

*Primary Examiner* — Alexander S Noguerola
(74) *Attorney, Agent, or Firm* — Stradley Ronon Stevens & Young, LLP

(57) ABSTRACT

The present invention relates to a system and method useful for determining the voltage of biological tissues and therefore to detect whether such tissues are cancerous.

15 Claims, 16 Drawing Sheets

(51) Int. Cl.
G01N 33/487 (2006.01)
A61B 5/00 (2006.01)
A61B 5/04 (2006.01)
G01N 33/483 (2006.01)
G01N 27/327 (2006.01)

(52) U.S. Cl.
CPC .............. A61B 5/05 (2013.01); G01N 27/403 (2013.01); G01N 33/483 (2013.01); G01N 33/48707 (2013.01); A61B 2562/0215 (2017.08); A61B 2562/0217 (2017.08); G01N 27/327 (2013.01)

(56) References Cited

U.S. PATENT DOCUMENTS

| | | | |
|---|---|---|---|
| 6,251,681 | B1 | 6/2001 | Davies et al. |
| 2001/0005137 | A1 | 6/2001 | Horie et al. |
| 2009/0253193 | A1 | 10/2009 | Gregory |
| 2012/0006694 | A1 | 1/2012 | Troy et al. |
| 2012/0165634 | A1* | 6/2012 | Lee .................. A61B 5/00 600/345 |
| 2012/0186998 | A1* | 7/2012 | Hermans ............ A61B 5/14865 205/780.5 |
| 2013/0211280 | A1 | 8/2013 | Gregory et al. |
| 2014/0127791 | A1 | 5/2014 | Foertsch et al. |

OTHER PUBLICATIONS

Potter et al., "A new approach to neural cell culture for long-term studies," Journal of Neuroscience Methods 110 (2001) 17-24 (Year: 2001).*

Geddes, "Optimum Electrolytic Chloriding of Silver Electrode," Med. & Biol. Engng. vol. 7, pp. 49-56, 1969 (Year: 1969).*

Wu et al., "A glue-based, screw-free method for implantation of intra-cranial electrodes in young mice," Journal of Neuroscience Methods 171 (2008) 126-131 (Year: 2008).*

Pedrotti et al., "Miniaturized Reference Electrodes with Miroporous Polymer Junctions," Electroanalysis 1996, 8, No. 7, pp. 673-675 (Year: 1996).*

Fajac et al., "Silver/silver chloride electrodes for measurement of potential difference in human bronchi," Thorax 1998:53:879-881 (Year: 1998).*

Abidjan, M.R. and Martin, D.C, "Experimental and theoretical characterization of implantable neural microelectrodes modified with conducting polymer nanotubes" Biomaterials. 2008 29(9):1273-83.

Adams, D.S. and Levin, M., "General principles for measuring resting membrane potential and ion concentration using fluorescent bioelectricity reporters" 2012(4):385-397.

Balog, J., "Intraoperative Tissue Identification Using Rapid Evaporative Ionization Mass Spectrometry" Sci Transl Med. 2013 5(194):194ra93.

Binggeli, R. and Cameron, I.L., "Cellular potentials of normal and cancerous fibroblasts and hepatocytes" Cancer Res. 1980 40(6):1830-5.

Binggeli, R. and Weinstein, R.C, "Membrane potentials and sodium channels: hypotheses for growth regulation and cancer formation based on changes in sodium channels and gap junctions" J Theor Biol. Dec. 21, 1986;123(4):377-401.

Chapman, D.L., The London, Edinburgh, and Dublin Philosophical Magazine and Journal of Science, 2010, 1913 25 (148) 475-481.

Chernet, B.T., and Levin, M., "Transmembrane voltage potential is an essential cellular parameter for the detection and control of tumor development in a Xenopus model" Dis Model Mech. 2013 6(3):595-607.

Cuzick. J. et al "Electropotential measurements as a new diagnostic modality for breast cancer" Lancet. 1998 352(9125):359-63.

Franks, W. et al., "Impedance characterization and modeling of electrodes for biomedical applications" IEEE Trans Biomed Eng 2005 52(7):1295-302.

Lobikin, M. et al., "Resting potential, oncogene-induced tumorigenesis, and metastasis: the bioelectric basis of cancer in vivo" Phys Biol 2012 9(6):065002.

McCaig, C.D., et al., "Electrical dimensions in cell science" J Cell Sci. 2009 122(Pt 23):4267-76.

Wu, W. et al "A method for voltage measurements of cancerous vs non-cancerous omentum" Conf Proc IEEE Eng Med Biol Soc. 2015:7514-7.

Yang, M. and Brackenbury, W.J., "Membrane potential and cancer progression" Front Physiol. 2013 4:185.

Zeuthen, T., "Tungsten (W) as electrode material: Electrode potential and small-signal impedances" Med Biol Eng Comput 1978 16(5):483-8.

* cited by examiner

SYSTEM AND METHOD FOR VOLTAGE MEASUREMENTS ON BIOLOGICAL TISSUES

CROSS-REFERENCE TO RELATED APPLICATIONS

This application is a 35 U.S.C. § 371 national phase application of PCT Application No. PCT/GB2016/052639, filed Aug. 25, 2016, which claims priority to Great Britain Application No. GB 1515115.2, filed Aug. 25, 2015, each of which is incorporated herein by reference in its entirety.

FIELD OF THE INVENTION

The present invention relates to a system and method useful for determining the voltage of biological tissues and therefore to detect whether such tissues are cancerous.

BACKGROUND TO THE INVENTION

Real-time diagnostics during surgery and in vivo monitoring of chemotherapy-induced tissue changes in the neo-adjuvant and adjuvant situation are two critical technologies in cancer treatments, which would enable individualized surgical treatment. Modalities which can offer information related to real-time tumour detection during surgery include the "iKnife" (intelligent Knife) (Balog et al., Science Translational Medicine, vol. 5, no. 194, p. 194ra93, 2013), whose operation is based on rapid evaporative ionization mass spectroscopy (REIMS). Fluorescent bioelectricity reporter (FBR) has been used to monitor a large number of cells simultaneously in vivo, and to track bioelectric gradients over relatively long time periods (despite cell movements and divisions) at a subcellular resolution level (Adams and Levin, Cold Spring Harbor Protocols, vol. 2012, no. 4, p. 385, 2012; Chernet and Levin, Disease Models & Mechanisms, vol. 6, no. 3, pp. 595.607, 2013). However, iKnife's wide clinical deployment calls for the building of detailed chemical spectrum databases while FBR has not been designed for clinical applications. Methods using electrical impedance spectroscopy (EIS) to differentiate between normal, pre-cancerous and cancerous tissues are known, for example the ZedScan technology from Zilico. Such methods exploit the different electrical resistivity of each specific tissue type based on its cellular structure. However, impedance measurement is an active measurement in that a current must be sent into the tissue or organ in order to detect the resulting voltage difference.

There is therefore a need in the art for an improved method of determining, during surgery, whether a tissue is cancerous or not.

SUMMARY OF THE INVENTION

The present inventors have devised a new system for determining the voltage of biological tissues, which can be used to detect whether such tissues are cancerous. The new system is a passive method, in the sense that no signal needs to be sent into the tissue. This has the advantage of being a much more simple system to use. Accordingly, in a first aspect the present invention provides a system for measuring the voltage of a tissue comprising:
 a tungsten electrode; and
 a silver/silver chloride electrode.

DETAILED DESCRIPTION OF THE INVENTION

The system of the first aspect of the invention is useful for measuring the voltage of a tissue. As will be understood by a person skilled in the art, the terms "voltage" and "potential difference" are equivalent and may be used interchangeably. The term "biopotential" is also used herein interchangeably with "voltage" and "potential difference".

The system of the first aspect of the invention comprises a tungsten electrode and a silver/silver chloride electrode.

The tungsten electrode typically acts as the working electrode in the system of the first aspect of the invention. Tungsten electrodes are known in the art and are commercially available. One example of a commercially available tungsten electrode is the D.ZAP electrode available from FHC Inc. (Bowdoin, Me.). Typically, at least part of the tungsten electrode is electrically insulated, for example using epoxylite insulation. In some embodiments, only the tip of the tungsten electrode is electrically conductive. This allows the electrode to take voltage measurements. The tungsten electrode can contain other materials in addition to tungsten. For example, part of the electrode can be made of other materials such as gold. In some embodiments, the part of the electrode that is not made of tungsten is a male connector that enables the whole electrode to be inserted in the female connector of a cable. FIG. 16 is a schematic of an exemplary tungsten electrode for use in the invention.

In some embodiments, the system may contain more than one tungsten electrode, for example 2, 3 or 4 tungsten electrodes. In some embodiments, where two tungsten electrodes are present, the first tungsten electrode measures the voltage of the tissue and the second tungsten electrode transfers the ground to the tissue.

The silver/silver chloride (Ag/AgCl) electrode typically acts as a reference electrode in the system, i.e. an electrode with a stable and well-known electrode potential. The electrode functions as a redox electrode and the reaction is between the silver metal (Ag) and its salt, silver chloride (AgCl, also called silver(I) chloride). The corresponding equations can be presented as follows:

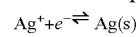
$$Ag^+ + e^- \rightleftharpoons Ag(s)$$

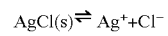
$$AgCl(s) \rightleftharpoons Ag^+ + Cl^-$$

or an overall reaction can be written:

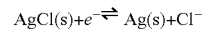
$$AgCl(s) + e^- \rightleftharpoons Ag(s) + Cl^-$$

Silver/silver chloride reference electrodes are commercially available and typically comprise a plastic tube electrode body. The electrode is typically a silver wire that is coated with a thin layer of silver chloride. This can be done either physically by dipping the wire in molten silver chloride or chemically by electroplating the wire in concentrated hydrochloric acid.

The tube within which the silver/silver chloride electrode is contained typically has a porous plug on one end, which allows contact between the field environment and the silver chloride electrolyte. An insulated lead wire typically connects the silver rod with measuring instruments. A voltmeter negative lead is typically connected to the test wire. The reference electrode typically contains a solution (an internal filling solution) of potassium chloride (KCl) to stabilize the silver chloride concentration. In some embodiments, the tube within which the silver/silver chloride electrode is contained also has an ion membrane at its tip. The ion membrane is typically a porous junction and can be made out of any suitable material, for example ceramic (such as frit) or porous glass (such as CoralPor (SCHOTT, Elmsford, N.Y.)). The ion membrane prevents the internal filling solution from leaking out to the external electrolyte (typically cell culture medium).

The silver/silver chloride electrode used in the invention may be a double junction reference electrode. In this embodiment, the electrode is separated from the external environment by a junction through which the electrolyte leaks. This can be effected, for example, by means of the tube which contains the silver/silver chloride electrode (and which may be filled with potassium chloride solution) being present inside another compartment, for example an additional tube. In this embodiment, both the first and the second tube can be sealed with a porous plug to allow the electrolyte to exit the tube. The signal can typically be detected without amplification because it is typically in the order of tens of millivolts. However, in some embodiments, the system further comprises an instrumentation amplifier. When present, the input terminals of the instrumentation amplifier are connected to the tungsten electrode and the silver/silver chloride reference electrode. The instrumentation amplifier records and amplifies potential differences between its terminals when the system is in equilibrium. One advantage of using an instrumentation amplifier is that it removes the common-mode noise from the input signal, so the output amplified signal has a higher signal-to-noise ratio (SNR). As a result, the voltage signals acquired are less vulnerable to noise. Another advantage of using an instrumentation amplifier is that it offers a very high differential mode input impedance (which allows efficient interfacing with the Ag/AgCl reference electrode). These features are useful when conducting the measurements in an electrically noisy hospital ward.

The outputs of the instrumentation amplifier can be connected to a data acquisition system for recording of data from the system. The data acquisition system typically converts the analogue output from the instrumentation amplifier into a digital signal.

The system of the first aspect of the invention is useful for measuring the voltage of a tissue. A "tissue" takes its normal meaning in the art, i.e. a collection of cells which together perform a particular function. The tissue is typically biological tissue, typically a sample of biological tissue taken from a human or animal subject. The tissue is typically a tissue that is suspected of being cancerous. For example, the tissue may have been removed from a patient by a biopsy or during surgery. For use in the invention, the tissue may be a single piece of tissue or a number of pieces of the same tissue. In one embodiment, the tissue is omentum. Omental tissue is of interest since omentum is the main location where ovarian cancer metastasizes. In other embodiments, the tissue is ovarian, rectal sigmoid, spleen, para-aortic lymph node or pelvic side wall tissue.

When the system of the invention is in use, at least the tungsten electrode is in direct contact with the tissue.

In some embodiments, the system of the first aspect of the invention comprises a medium. Typically, the medium is in contact with at least the housing of the silver/silver chloride electrode. This has the advantage that the silver/silver chloride reference electrode is not in direct contact with the tissue, which avoids contamination of the tissue by chloride ($Cl^-$) from the silver/silver chloride reference electrode and contamination of the silver/silver chloride reference electrode by the blood/liquids coming from tissue. In some embodiments, where the silver/silver chloride electrode is a double junction reference electrode, the outer compartment or tube is filled with the medium.

In some embodiments, the medium is also in contact with the tissue whose voltage is being measured using the system.

The medium is typically a cell culture medium but can also be any other electrolyte, for example saline solution. The medium typically supplies background ions in order to carry out the voltage measurement.

Any suitable cell culture medium can be used. Cell culture media are known and are commercially available, for example the RPMI 1640 cell culture medium from Life Technologies (Carlsbad, Calif.), Dulbecco's Modified Eagle medium (DMEM). In some embodiments, the cell culture medium contains additional compounds such as drugs. For example, the cell culture medium can contain one or more antibiotics (such as penicillin or streptomycin) in order to prevent bacterial contamination. In some embodiments, the cell culture medium can also be supplemented with foetal calf serum and/or L-Glutamine.

The system of the first aspect of the invention can also comprise further components, for example to hold the electrodes in position. For example, the system can further comprise one or more pipette tips. In some embodiments, one or both of the tungsten electrode and the silver/silver chloride reference electrode are held in place using a pipette tip.

In some embodiments, one or more of the pipette tips has a plug. The purpose of the plug is to impede the movement between the external solution and the internal filling solution while maintaining electrical contact between the working and the reference electrode. The plug can be made of any suitable material, for example tissue paper, or can be an ion membrane.

The system of the first aspect of the invention can also comprise a container such as a beaker, in which the medium is held. The other components of the system can then be placed in contact with the medium by inserting them into the container.

The system of the first aspect of the invention can also comprise clamps or other supports to hold the electrodes and the other components of the system in place.

In one embodiment of the invention, as shown in FIG. 1, a medium such as a cell culture medium is present in the system. Typically, at least the housing of the silver/silver chloride electrode is in contact with the medium, and the tungsten electrode is in contact with a tissue sample that is in contact with the medium. Typically, the tungsten electrode is in contact with the surface of the tissue (and in some embodiments, the tip of the tungsten electrode pierces the surface of the tissue), but the tungsten electrode is not in contact with the medium. In this embodiment, the tissue sample can be held in place, for example, using a pipette tip, which can be immersed in the medium by means of placing the pipette tip into a suitable vessel containing the medium. The silver/silver chloride electrode can also be held in place using, for example, a pipette tip. Typically, the pipette tips used for this purpose have a plug. In this embodiment, both the housing of the silver/silver chloride electrode and the tissue are in contact with the medium, but the tungsten electrode is not in contact with the medium.

In another embodiment of the invention, as shown in FIG. 7, the housing of the silver/silver chloride electrode is in contact with the medium (for example by means of placing the silver/silver chloride electrode, including its housing, in a pipette tip which contains the medium). The medium is therefore held in place in a container (for example a pipette tip) which contains a barrier (plug) preventing direct contact between the medium and the tissue. Another part of the tissue is in contact with the tungsten electrode. In this embodiment, the moisture in the tissue creates an ionic bridge between the silver/silver chloride electrode and the tungsten electrode.

In some embodiments, the system of the invention is incorporated into a portable device (or pen) that is small enough to be used, for example, during surgery. This means that the surgeon is able to determine during the surgery whether the tissue is cancerous or not and can take the necessary clinical decision, for example whether to remove that tissue or not.

In some embodiments, the device directly interfaces with the tissue without the presence of any medium at the point of measurement. This can be done by means of one or more of the electrodes coming into direct contact with the tissue when in use. Typically, the electrode(s) that come into direct contact with the tissue when in use is the one or more tungsten electrodes.

In the device of the invention, the Ag/AgCl electrode is typically a double junction reference electrode. In one embodiment, the Ag/AgCl electrode is present inside a chamber that contains medium such as cell culture medium. This has the advantage that chloride ($Cl^-$) which is contained in the Ag/AgCl reference electrode is slowly mixed with the media of the chamber and not with the tissue. This avoids contamination of the tissue by chloride and contamination of the Ag/AgCl reference electrode by the blood/liquids coming from tissue. This chamber is typically filled with fresh medium at the beginning of each experiment.

The device of the invention can also contain other components, for example a printed circuit board (PCB), which can be incorporated in the interior of the device. The role of the PCB can include receiving the voltage signals from the working and reference electrodes, recording the voltage difference between them, amplifying it (for example with a selectable gain of 4 or 10), converting it from analog to digital and/or sending it wirelessly to a computer by means of a short-range radio module. A suitable connector, which is located on the board, may permit an additional wired connection to a data acquisition system, for example Powerlab. The device is typically enclosed in a housing which can be manufactured using any suitable materials. In one embodiment, the housing is manufactured by 3D printing.

A device of the invention typically has the advantage of being portable and wireless. This enables the in-situ read-out of cancerous and healthy tissue voltage differences (e.g. during surgery) and the wireless transmission of the recorded data to a nearby station, for subsequent storage and assessment of the recorded data.

An exemplary device of the invention is shown in FIGS. 13, 14 and 15.

The system of the first aspect of the invention is useful for measuring the voltage of a tissue. Accordingly, in a second aspect the present invention provides a method for measuring the voltage of a tissue, comprising contacting a sample of the tissue with the system of the first aspect of the invention and detecting the voltage of the tissue sample.

The method of the second aspect of the invention can be used to measure the voltage of any tissue, as described herein in relation to the first aspect of the invention. The method of the second aspect of the invention is not intended for use in measuring the voltage of a single cell.

The present inventors have surprisingly found that cancerous tissue has a lower voltage than non-cancerous tissue. The voltage of the tissue can therefore be used to determine whether tissue is cancerous or not. Accordingly, in a third aspect the present invention provides a method for detecting cancerous tissue, comprising contacting a sample of the tissue with the system of the first aspect of the invention and detecting the voltage of the tissue sample, and comparing the voltage of the tissue sample to the voltage of a control sample.

The control sample used in the third aspect of the invention is typically a sample of tissue that is known to be non-cancerous. Typically, the control sample is a sample of the same type of tissue as the tissue that is being tested. Typically, the control sample is taken from the same patient as the tissue that is being tested. For example, the tissue to be tested and the control sample can be taken from the same patient during surgery. A surgeon will be aware of which tissue appears to be cancerous and which tissue appears to be healthy, and this knowledge can be used to decide on a sample to be taken of potentially cancerous and also non-cancerous tissue.

A decreased voltage of the tissue sample compared to the control sample is indicative of cancer. Typically, a statistically significant decrease in voltage is indicative of cancer. Statistical significance can be tested using any suitable mathematical model, for example the Mann-Whitney U-test or t-test paired statistical tests, the Wilcoxon Sign Rank test and Sign test, and suitable significance levels to be used (for example $p<0.05$, $p<0.03$ or $p<0.01$) will be within the knowledge of a skilled person.

In one embodiment of the second and third aspects of the invention, the tissue sample is in contact with the tungsten electrode and a medium is present that is in contact with the tissue and the silver/silver chloride electrode.

In another embodiment of the second and third aspects of the invention, the tissue sample is in contact with the tungsten electrode and the silver/silver chloride electrode and a medium is present that is in contact with the silver/silver chloride electrode.

Preferred features for the second aspect of the invention are as for the first aspect mutatis mutandis.

Exemplary embodiments of the first aspect of the invention are shown in FIGS. 1 and 7.

In the embodiment of the invention shown in FIG. 1, the silver/silver chloride reference electrode is present in a tube which also contains a solution of potassium chloride. The tube in which the silver/silver chloride reference electrode is housed is in contact with medium and has an ion membrane at its tip. The silver/silver chloride reference electrode is held in place using a pipette tip which has a plug. The tungsten electrode is in contact with a tissue sample under investigation (in this instance omental tissue), and the tissue sample is in direct contact with the medium. The tungsten electrode is only in contact with the surface of the tissue and is not in contact with the medium. The tungsten electrode and the tissue sample are held in place using a pipette tip. The silver/silver chloride reference electrode and the tungsten electrode are connected to an instrumentation amplifier which is in turn connected to a data acquisition system.

In the embodiment of the invention shown in FIG. 7, the silver/silver chloride reference electrode is present in a tube which also contains a solution of potassium chloride. The tube in which the silver/silver chloride reference electrode is housed is in contact with medium and has an ion membrane at its tip. The silver/silver chloride reference electrode is held in place using a pipette tip which has a plug. The pipette tip contains cell culture medium, which is in contact with the housing of the silver/silver chloride reference electrode. The plug of the pipette tip is in contact with part of the tissue and prevents direct contact of the tissue with the medium. Another part of the tissue is in contact with the tungsten electrode. The silver/silver chloride reference electrode and the tungsten electrode are connected to an instrumentation amplifier which is in turn connected to a data acquisition system.

BRIEF DESCRIPTION OF THE DRAWINGS

The present invention will now be further described by way of reference to the following Examples which are present for the purposes of illustration only. In the Examples, reference is made to a number of Figures in which.

The dimensions illustrated in the Figures are exemplary only. The Figures are not drawn to scale. It will be appreciated that the dimensions and materials of the system of the invention can be varied as desired.

EXAMPLES

Example 1—Measuring the Voltage of Paired Cancerous and Non-Cancerous Tissue Using Experimental Setup "With Medium"

Experimental Setup

A. Electrode Surface Potential Considerations

Figure 1:
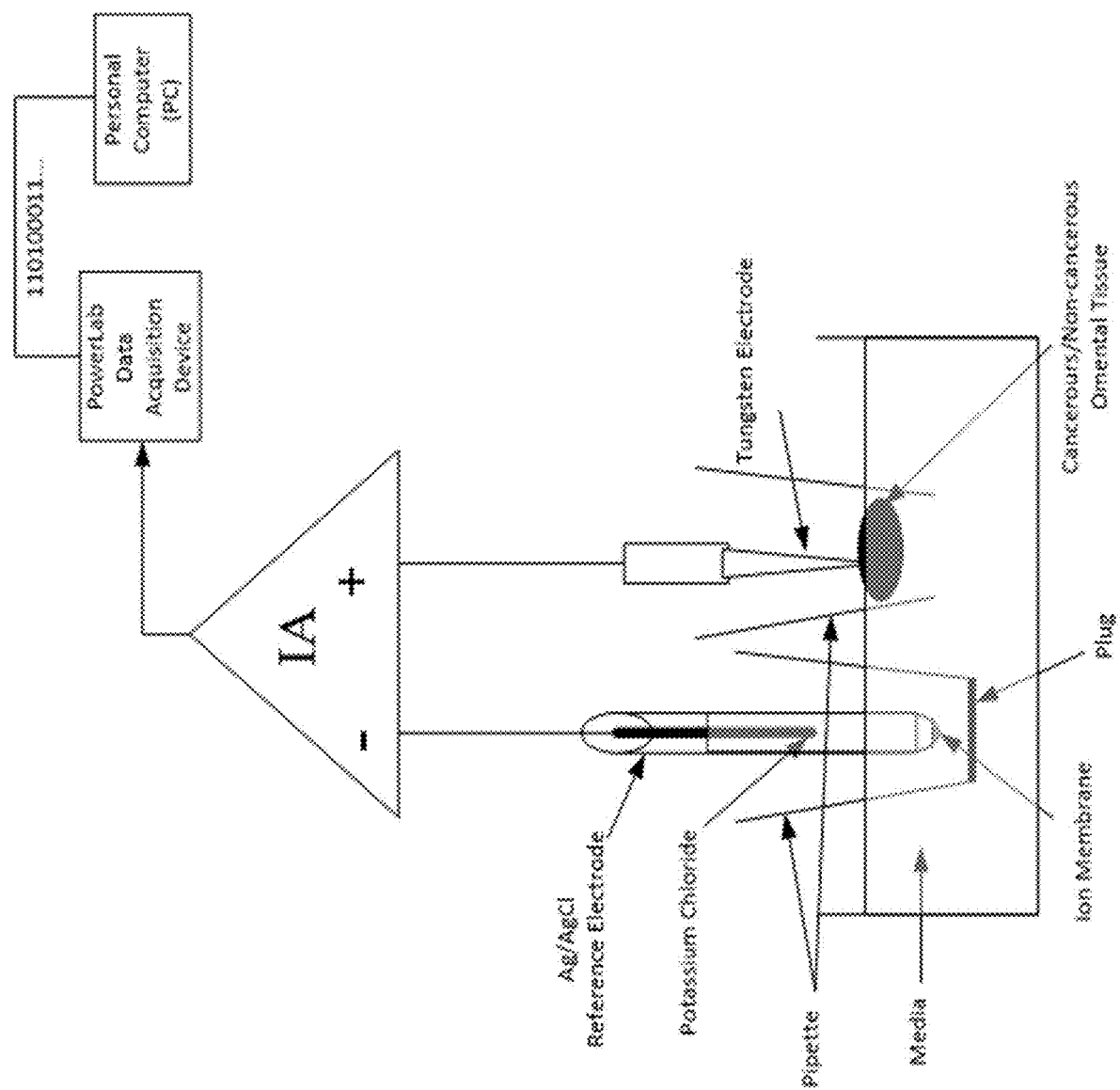
FIG. 1 is a schematic of one arrangement of the system of the invention, in which the housing of the silver/silver chloride reference electrode and the tissue sample is in contact with a medium. This is referred to herein as the experimental setup "with medium". In this Figure and also in FIGS. 7 and 10, the IA polarity [the plus (+) and minus (−) inputs of the IA] is indicative only.

FIG. 1 illustrates the experimental setup used for the recording of tissue voltage. It incorporates an instrumentation amplifier (IA) whose input terminals are connected to: i) a Ag/AgCl electrode in contact with the media within which the cancerous or non-cancerous omentum is touching, and ii) an FHC D.ZAP tungsten electrode with a metal-tip diameter of 0.3 mm. The tungsten electrode is in contact with the tissue sample which is placed within a standard 1 ml pipette tip placed in a beaker containing media; the electrode is not in direct contact with the media in the beaker. The Ag/AgCl electrode realises a high-impedance liquid junction path. The IA records and amplifies potential differences between its terminals when the system is in equilibrium. The amplified potential difference is subsequently converted to the digital domain by means of a data acquisition system.

Figure 2:
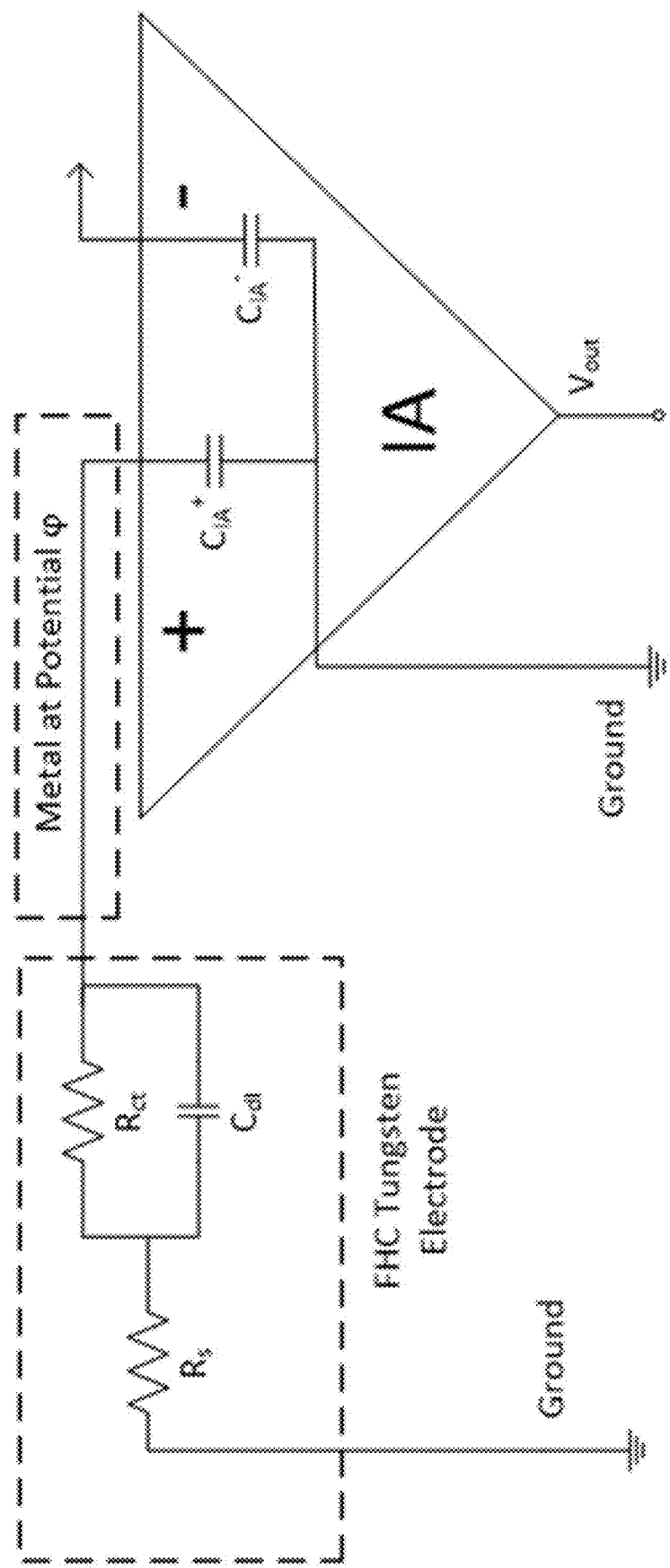
FIG. 2 is a simplified DC equivalent of the setup shown in FIG. 1.

FIG. 2 illustrates a simplified DC equivalent of the setup shown in FIG. 1 which in practice records the difference between the potential developed on the surface of the tungsten electrode (when in contact with the tissue) and the Ag/AgCl electrode. During measurement the media corresponds to electrical ground. The double-layer capacitance of the tungsten-electrolyte (media) equivalent is denoted by $C_{dl}$, its charge transfer by $R_{ct}$ while its solution resistance is denoted by $R_s$. Bearing in mind that the recorded potential difference is practically of a DC nature, the IA equivalent circuit degenerates into two input capacitors, $C_{IA}^+$ and $C_{IA}^-$, associated with the IA's respective input terminals. When tissue voltage measurement takes place, a surface potential value $\varphi$ is associated with a total charge $$Q_{tot} = A\sigma = AC'_{dl}\phi + C_{IA}^+\phi \tag{1}$$

developed across the capacitance $C_{IA}^+$ and $AC_{dl}'$ where $C_{dl}'$ denotes double-layer capacitance per unit area, A is the electrode-electrolyte interface area and σ denotes the surface charge density at the interface. However $C_{dl}'$ can be determined as (W. Franks et al., *Biomedical Engineering, IEEE*

Transactions on, vol. 52, no. 7, pp. 1295-1302, 2005 and M. R. Abidian and D. C. Martin, *Biomaterials*, vol. 29, no. 9, pp. 1273-1283, 2008):

$$\frac{1}{C'_{dl}} = \frac{1}{C_H} + \frac{1}{C_G} = \frac{d_{OHP}}{\varepsilon_0 \varepsilon_r} + \frac{L_D}{\varepsilon_0 \varepsilon_r \cosh\left(\frac{z\phi}{2U_t}\right)} = \frac{1}{\theta} \quad (2)$$

where $d_{OHP}$ denotes the double-layer capacitor thickness, $\varepsilon_0 \varepsilon_r$ denotes the electrolyte's relative permittivity, $L_D$ denotes the Debye length, z denotes ionic chemical valence in the electrolyte and $U_t$ denotes the thermal voltage. Considering (1) and (2) yields:

$$\phi = \frac{\sigma}{\theta + \frac{C_{IA}^+}{A}} \quad (3)$$

Bearing in mind (2), note that the quantity φ appears on both sides of the transcendental equation (3). It should be stressed that the derivation of the DC equivalent of the setup shown in FIG. 1 relies upon the strong assumption that the electrode-(electrolyte plus tissue) interface (see FIG. 1) can be described, at least to a first order, by the Gouy (R. Reeves, "The electrical double layer: The current status of data and models, with particular emphasis on the solvent," in *Modern Aspects of Electrochemistry*. Springer, 1974, pp. 239-368)-Chapman (D. L. Chapman, *The London, Edinburgh, and Dublin Philosophical Magazine and Journal of Science*, vol. 25, no. 148, pp. 475-481, 1913) double-layer theoretical approach resulting from the combination of Poisson equation of electrostatics and Boltzmann statistics (W. Franks et al., *Biomedical Engineering, IEEE Transactions on*, vol. 52, no. 7, pp. 1295-1302, 2005).

Moreover it should also be stressed that the finally recorded difference value is not equal to φ since the measured voltage value is also affected by the Ag/AgCl reference electrode potential.

B. Media Only Voltage Measurements

In this subsection the role of the area A and the capacitance $C_{IA}^+$ is investigated by means of the setup of FIG. 1 when the tissue sample is absent, i.e. when only media is used. The motivation for this stems from the need to confirm qualitatively the dependence of the recorded potential difference upon φ which, in turn according to our aforementioned strong assumption, depends upon the area A and the capacitance $C_{IA}^+$.

Figure 3:
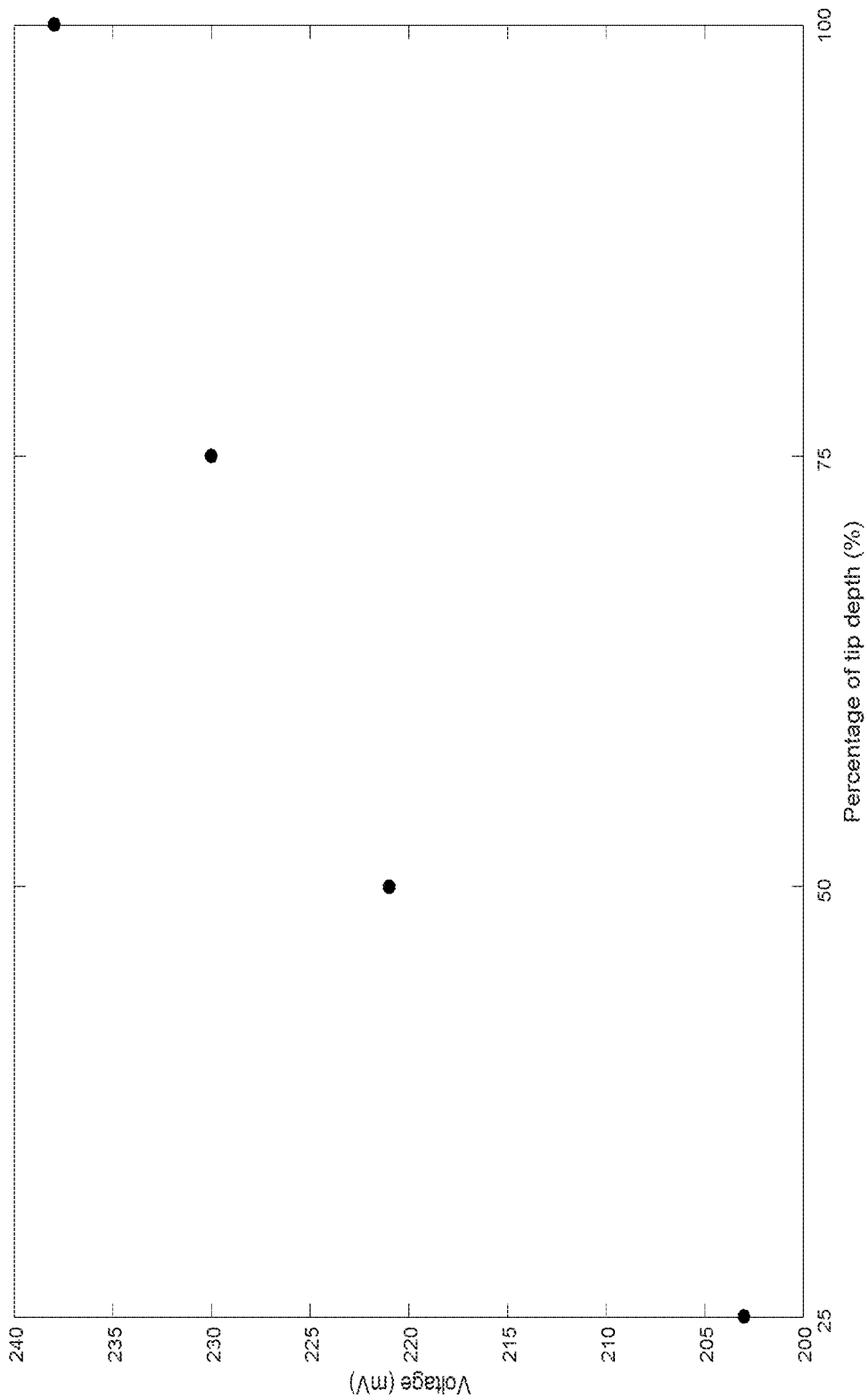
FIG. 3 shows the variation of measured potential difference with tungsten electrode tip depth (media only measurement).

FIG. 3 illustrates the recorded potential difference when the tip of the tungsten electrode (the remainder of the electrode is insulated) is immersed progressively by 25%, 50%, 75% and 100% of its length within RPMI-1640 medium (Life Technologies, Carlsbad, Calif.). Observe that the recorded potential difference increases with depth. As the electrode's depth increases the electrode's area interfacing with the media also increases. The measurements of FIG. 3 reveal a saturating trend for increasing area values. Confirm a similar trend for (3): bearing in mind that the quantity θ is bounded, the quantity φ reaches the saturation value $\sigma/C_{dl}'$ when A takes large values.

Despite the fact that the capacitances $C_{IA}^+$ and $C_{IA}^-$ are not part of the immediate electrode-specimen environment, they become part of the measurement process. Recording of the measured potential difference values for different $C_{IA}^+$ values (i.e. for different IAs) and for the same tip depth would be impractical. Instead it is straightforward to apply a capacitor in parallel with $C_{IA}^+$ and investigate its effect upon the measured potential difference for a given tip depth (i.e. for a given A value). Such a capacitor was applied haptically and the potential difference was recorded before and after the application of the haptic capacitor. The recorded potential difference was reduced from just over 200 mV to around 170 mV when the haptic capacitor was applied. Equation (3) reveals a similar behaviour for φ when the apparent $C_{IA}^+$ value increases while the other terms remain constant.

The surface charge density σ in equations (1) and (3) should depend upon the microstructural characteristics of the specimen under test which is part of the electrode-(electrolyte plus tissue specimen) interface (see FIG. 1). In order to investigate the role of σ during measurement, the RPMI-1640 media was diluted progressively by means of deionised water. The recorded potential difference value decreased with decreasing media concentration (and thus decreasing σ) values and for the same electrode tip depth. Confirm from (3) that decreasing σ values lead to decreasing surface potential values.

Based on these results and taking into consideration that the microstructures of cancerous and non-cancerous omentum differ (M. Lobikin et al., *Physical Biology*, vol. 9, no. 6, p. 065002, 2012) (which might lead to different a values), it was theorised that the setup of FIG. 1 might prove useful in differentiating between the two types of tissue by recording a different potential difference value for each case. The next section investigates the potential of the setup of FIG. 1 in detecting such tissue voltage differences.

Measured Results

Ovarian cancer is one of the leading gynaecological cancers in the UK. Around 7000 women are diagnosed every year. Omental tissue was chosen as the testing specimen since omentum is an organ that stores lipids and regulates peritoneal fluid and is the main location where ovarian cancer metastasizes. An omentectomy is normally performed as a surgical treatment for ovarian cancer.

All omentum specimens used were excised during cytoreductive surgery and measurements were carried out no later than half an hour. Appropriate tissue collection ethical approval and approval for experiments were set in place. The protocol for the collection of cancerous and non-cancerous tissue potential difference data was designed as follows:

1. Bring the RPMI-1640 tissue culture media to room temperature.
2. Place the Ag/AgCl reference electrode in a 1 ml pipette which is fixed by an iron stand. Fix the tungsten working electrode with the same iron stand.
3. Place an omental specimen of appropriate size in a separate 1 ml pipette tip. Fix the pipette tip containing tissue in an iron stand and place the lower part of tip into a beaker containing the RPMI-1640 tissue culture media. Place the tungsten electrode into the tissue.
4. Connect both electrodes to the customized IA board (a 10-channel especially built instrument containing AD8420 IAs), whose outputs are connected to the data acquisition system.
5. Record data for a minimum of 2 minutes until the value stabilises.
6. Repeat the recording for different specimens or different spots of the same specimen.
7. Dispose of the specimen in an appropriate way.

Potential-difference data have been recorded in accordance with the above protocol from media only, non-cancerous omentum samples and cancerous ones. The results are shown in FIGS. 4, 5 and 6.

Figure 4:
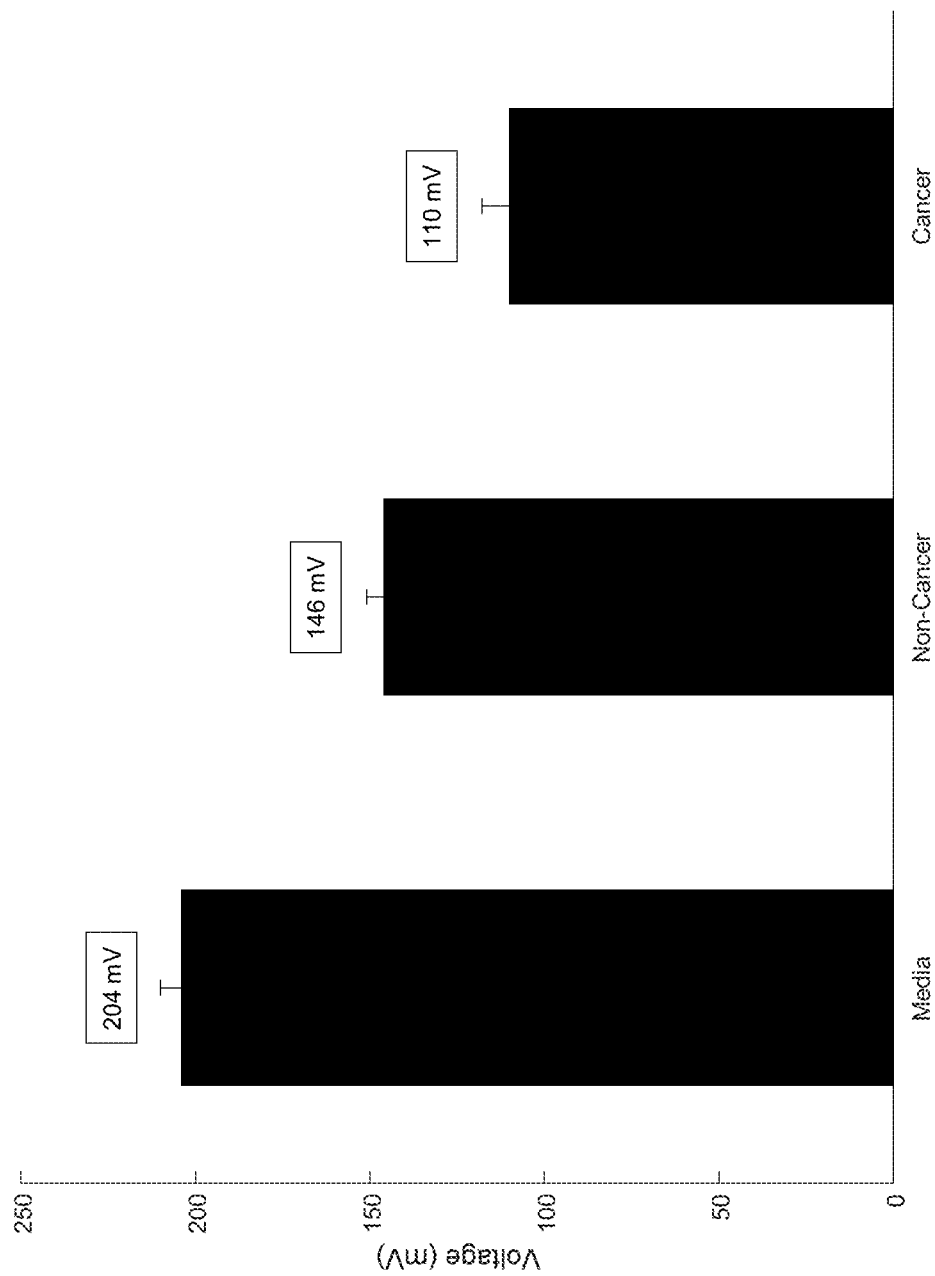
FIG. 4 shows the results of experiments to determine the voltage of medium alone, cancerous and non-cancerous tissue.
Figure 5:
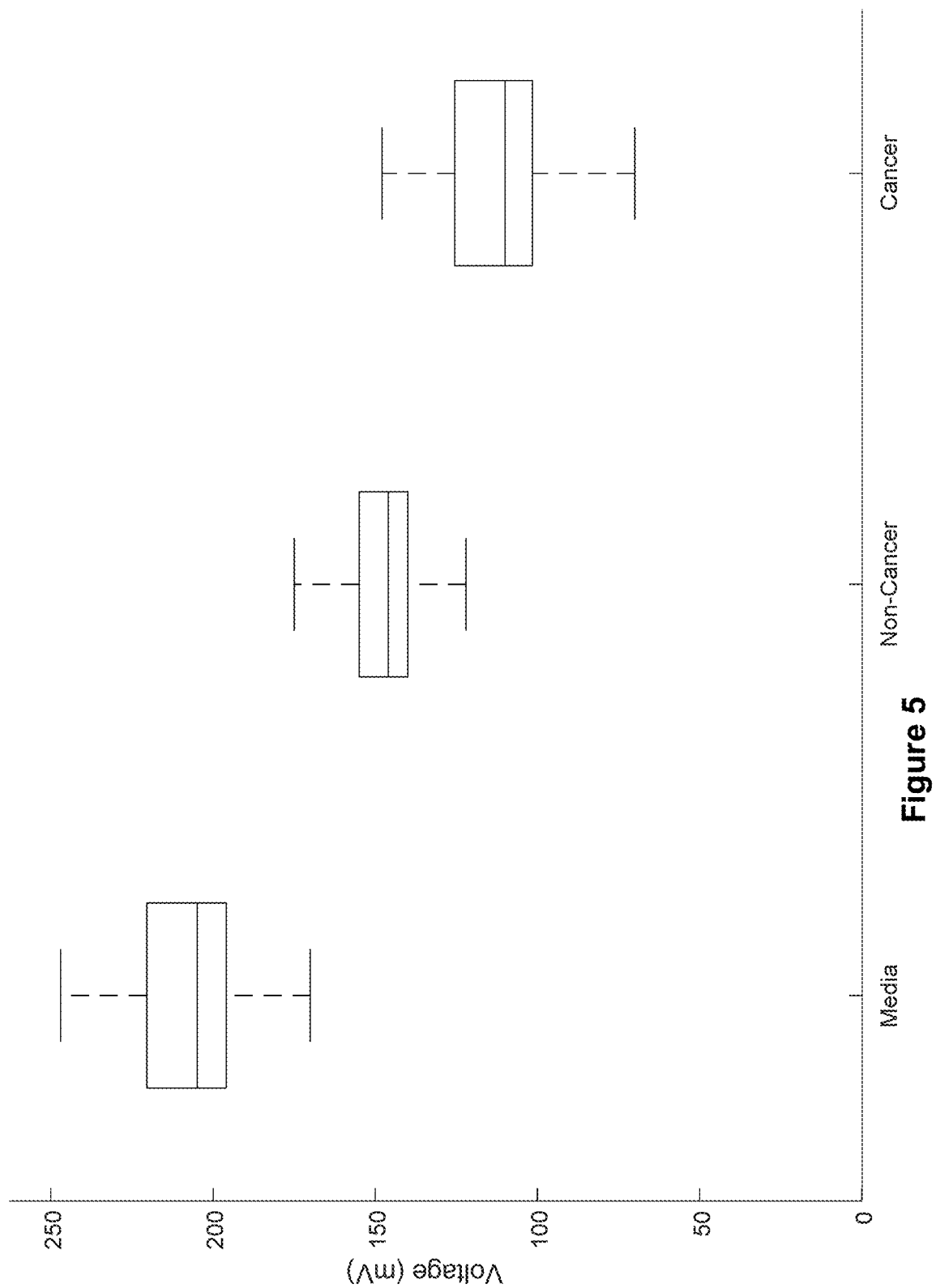
FIG. 5 is a box-and-whisker plot depicting the quartiles of the voltage values shown in FIG. 3.
Figure 6:
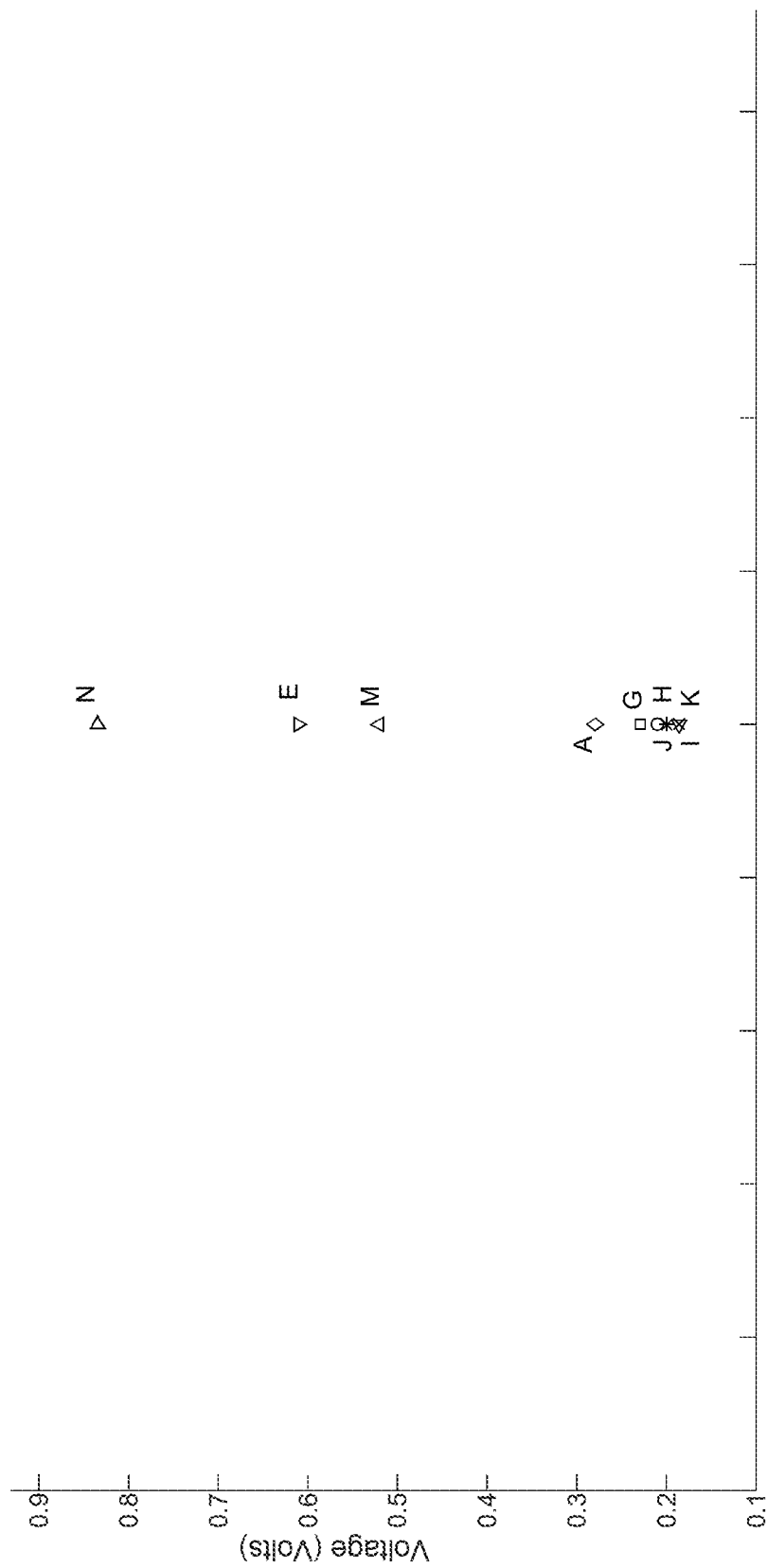
FIG. 6 shows the difference in voltage values between the non-cancerous and cancerous omentum in individual patients.

For the experiments reported in FIGS. 4, 5 and 6, omentum samples were taken from 15 different patients. As can be seen from FIG. 4, the voltages were higher in non-cancerous tissue than in cancerous tissue. The results were significant at $p<0.05$ using both Mann-Whitney U-test and t-test paired statistical tests. FIG. 5 is a box-and-whisker plot depicting the quartiles of the voltage values shown in FIG. 4. FIG. 6 shows the difference in voltage values between the non-cancerous and cancerous omentum in individual patients. Each shape/letter in FIG. 6 represents an individual patient. The reported voltage values in FIG. 6 are the amplified (×G) ones, where G (=10) is the gain of the amplifier. This Figure therefore refers to voltages in volts, whereas FIGS. 4 and 5 refer to voltages in millivolts.

Conclusions

It should be stressed that the difference in voltage level values between the cancerous and the non-cancerous case corresponds to "difference of potential differences". Given that the Ag/AgCl electrode and the media type is common in all experiments, it can be concluded that the recorded voltage level differences reflect a difference in tissue properties.

Example 2—Measuring the Voltage of Paired Cancerous and Non-Cancerous Omental Tissue Using Experimental Setup "Without Medium"

Experimental Setup

Figure 7:
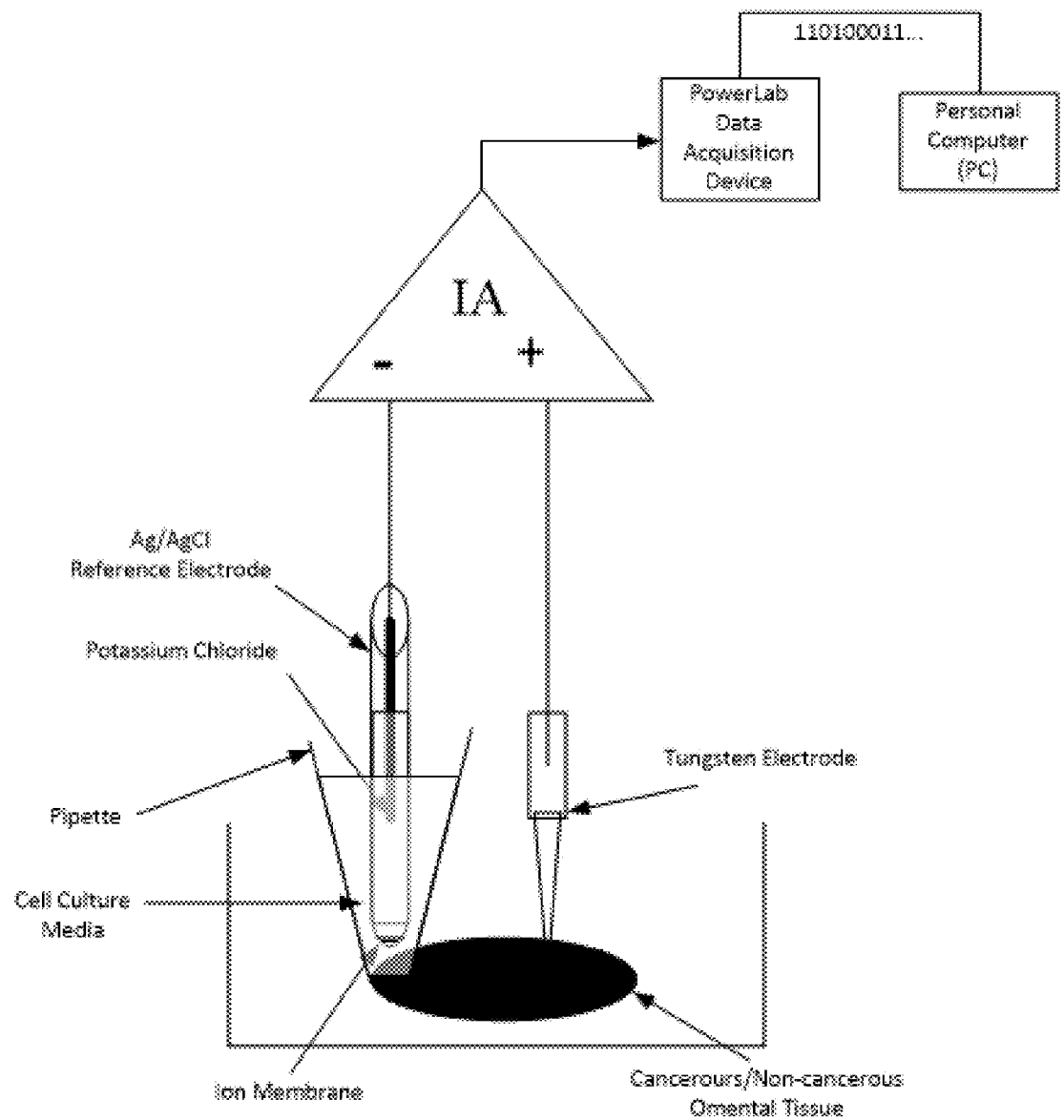
FIG. 7 is a schematic of another arrangement of the system of the invention, in which only the housing of the silver/silver chloride electrode is in contact with a medium. This is referred to herein as the experimental setup "without medium".

In these experiments, the experimental setup shown in FIG. 7 was used.

Measured Results

Figure 8:
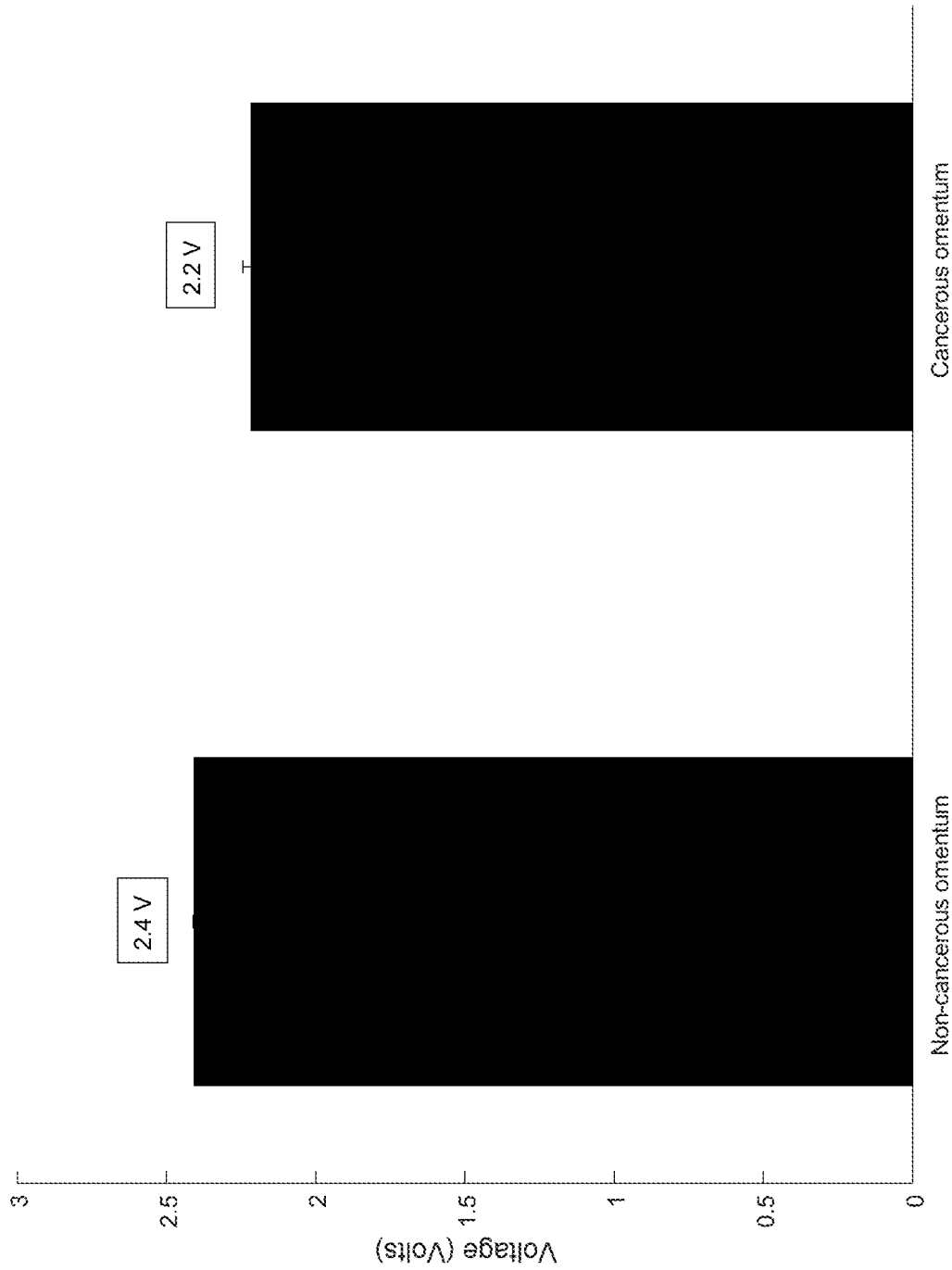
FIG. 8 shows the results of experiments to determine the voltage of cancerous and non-cancerous tissue using the experimental setup "without medium".

The results of the experiments are shown in FIG. 8. As can be seen from the Figure, the cancerous tissue had a lower voltage than the non-cancerous tissue.

Example 3—Measuring the Voltage of Various Tissues

Experimental Setup

The voltage of medium alone, non-cancerous omentum and various cancerous tissues (omentum, right ovary, rectal sigmoid, spleen, para-aortic lymph node, pelvic side wall) was tested. In these experiments, the experimental setup shown in FIG. 1 was used.

Measured Results

Figure 9:
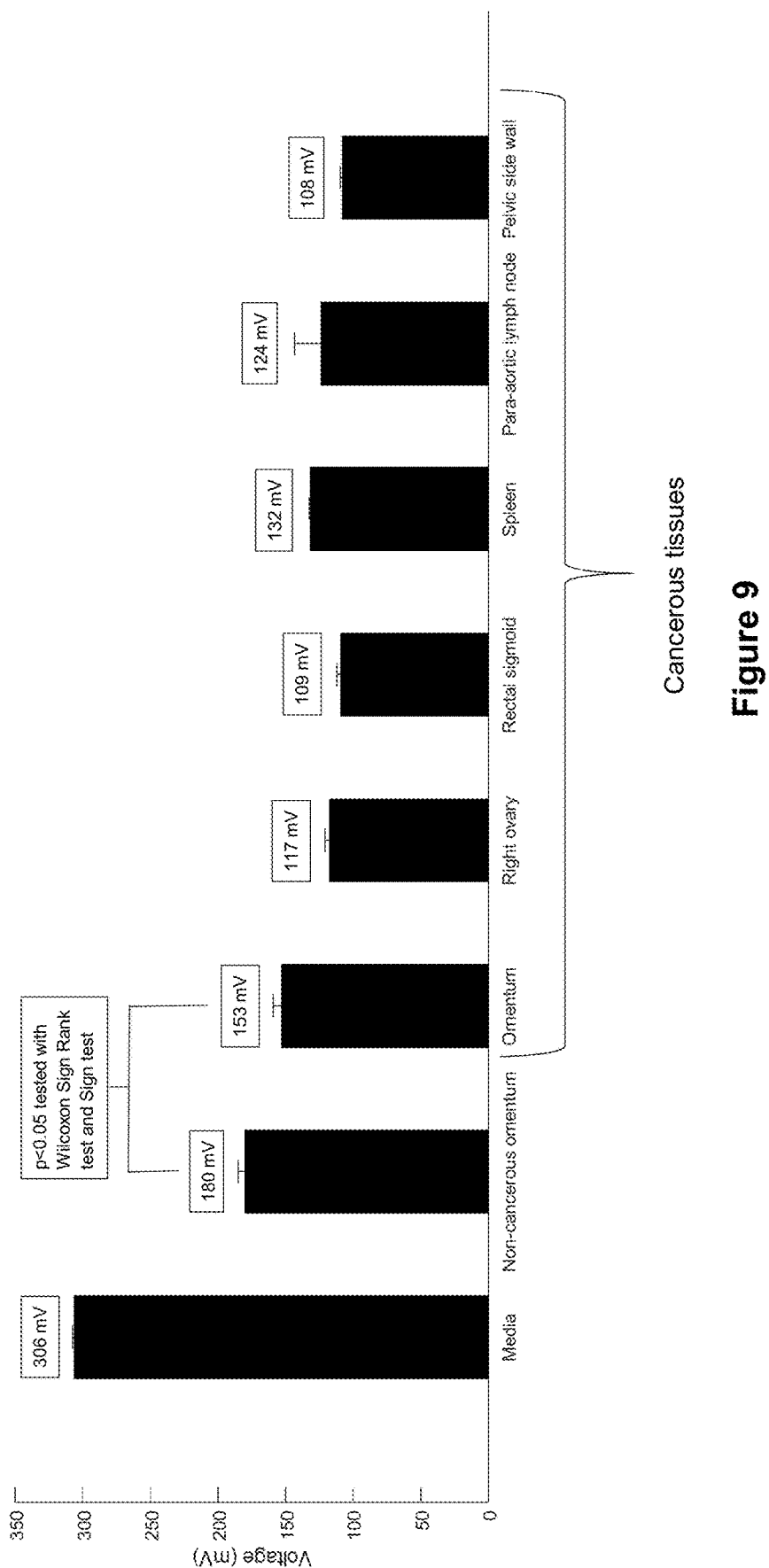
FIG. 9 shows the results of experiments to determine the voltage of medium alone, non-cancerous omental tissue and various different types of cancerous tissue using the experimental setup "with medium".

The results of the experiments are shown in FIG. 9. As can be seen from the Figure, the various cancerous tissues had low voltages.

Example 4—Measuring Voltage in Materials Characterized by Different Densities or Different Ion Contents Background The goal of this experiment was to examine if the method we have developed for taking biopotential measurements in human tissues using a tungsten working electrode and a double junction Ag/AgCl reference electrode can identify voltage differences in materials characterized by different densities or different ion contents. We manipulated material density by changing agar concentration in a gel. Moreover, we manipulated material ion content by changing media concentration in a gel. Based on this strategy, we produced two sets of gels. In the first set, the gels contained the same concentration of agar [3% (w/v)] but different media concentrations. The first gel contained 100% (v/v) media (30 mL media), the second 50% (v/v) media (15 mL deionized water and 15 mL media) and the third 10% (v/v) media (27 mL deionized water and 3 mL media). In the second set, the gels contained the same media concentration (10 mL) but different agar concentrations. The first gel contained 1% (w/v) agar (0.1 g), the second 2% (w/v) agar (0.2 g), the third 3% (w/v) agar (0.3 g) and the forth 5% (w/v) agar (0.5 g).

Experimental Setup

Figure 10:
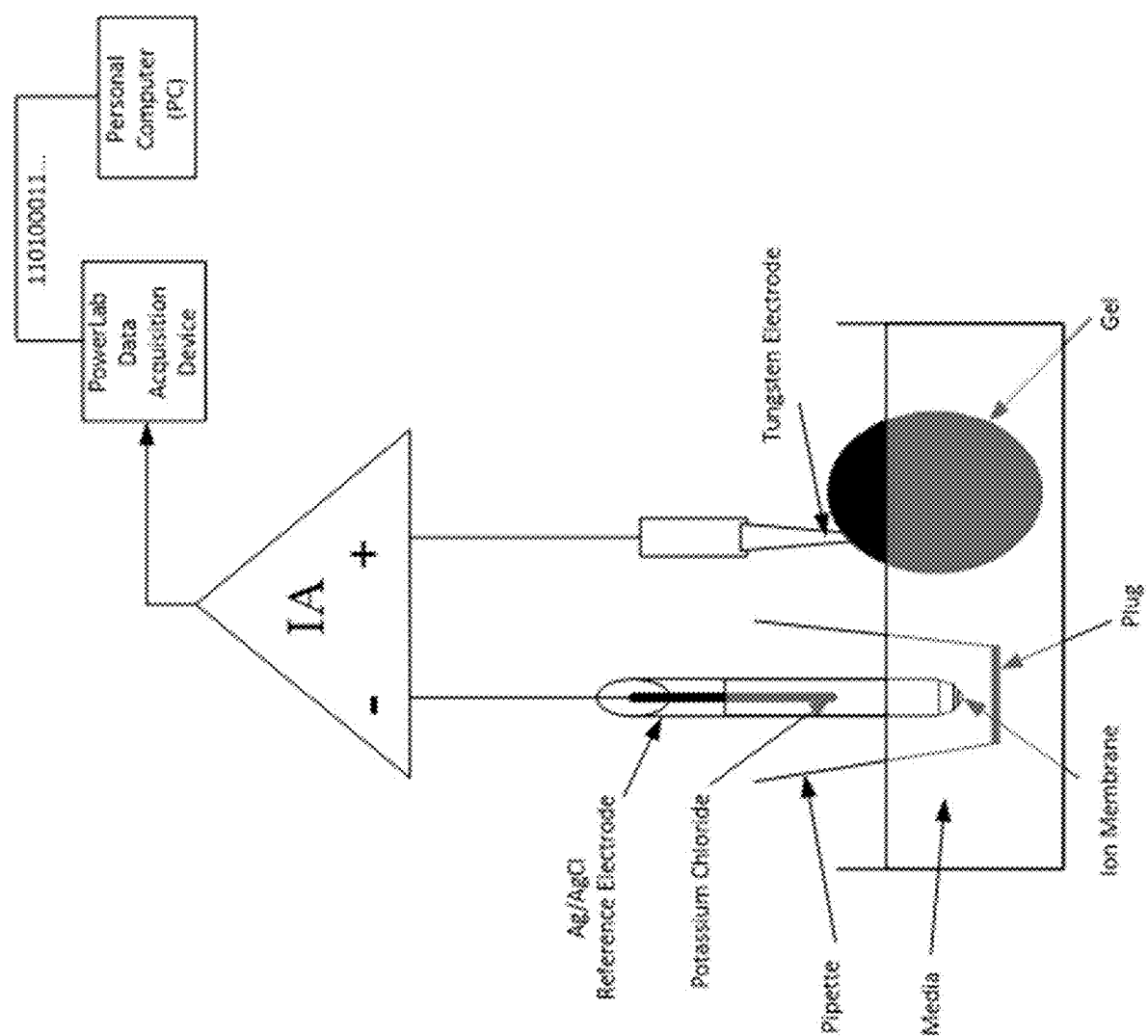
FIG. 10 is a schematic of the experimental setup used for experiments to determine the voltage of gels characterised by the same densities but different ion contents and gels characterised by the same ion contents but different densities. This experimental setup is very similar to the one shown in FIG. 1, except that the gel replaces the tissue whose voltage is to be determined and that there is no pipette holding the tungsten electrode in place.

In these experiments, the experimental setup shown in FIG. 10 was used.

Results

Figure 11:
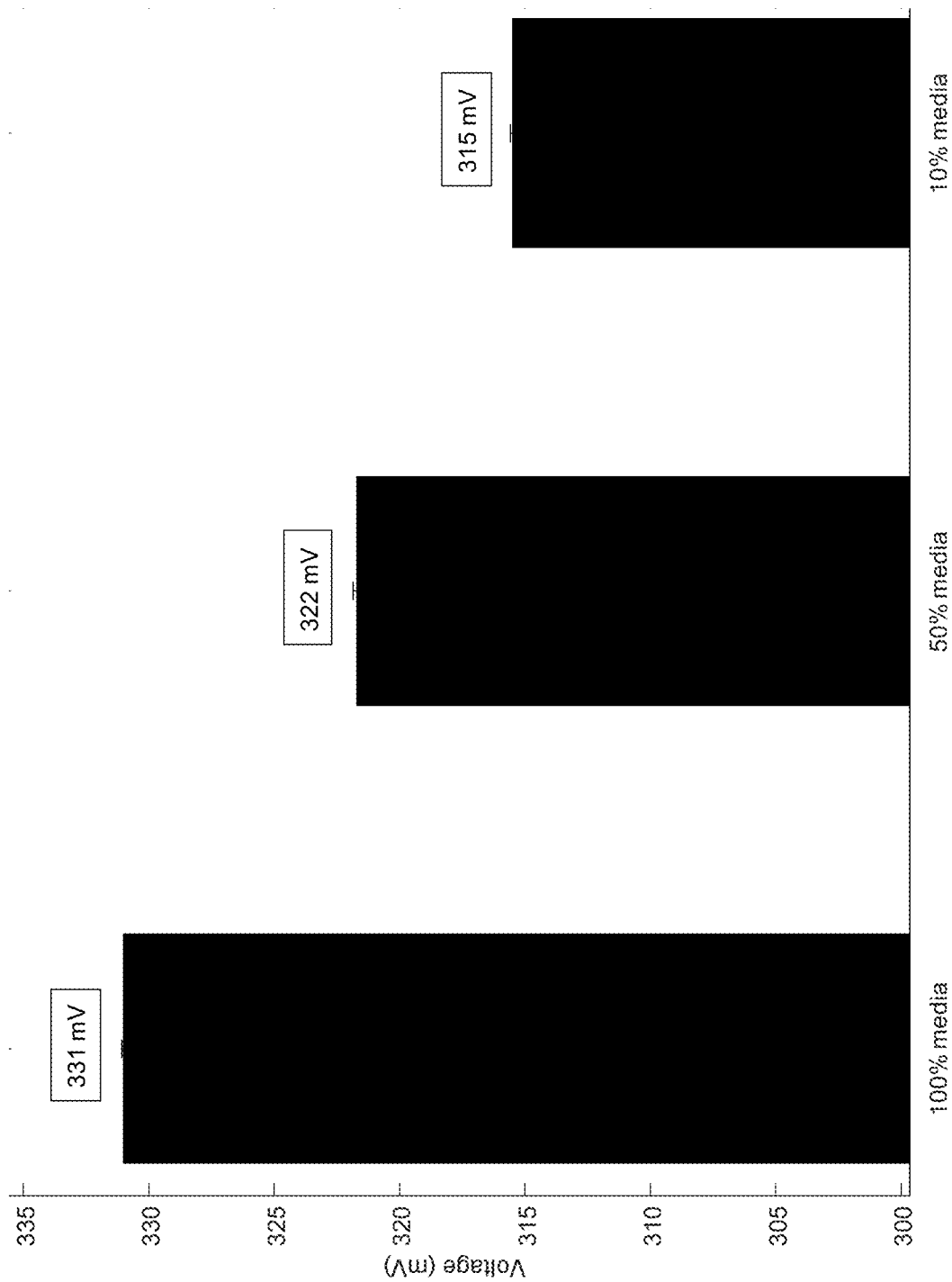
FIG. 11 shows the results of experiments to determine the voltage of gels characterised by the same densities but different ion contents (same agar concentration but different medium concentration).
Figure 12:
FIG. 12 shows the results of experiments to determine the voltage of gels characterised by the same ion contents but different densities (same medium concentration but different agar concentration).
Figure 13:
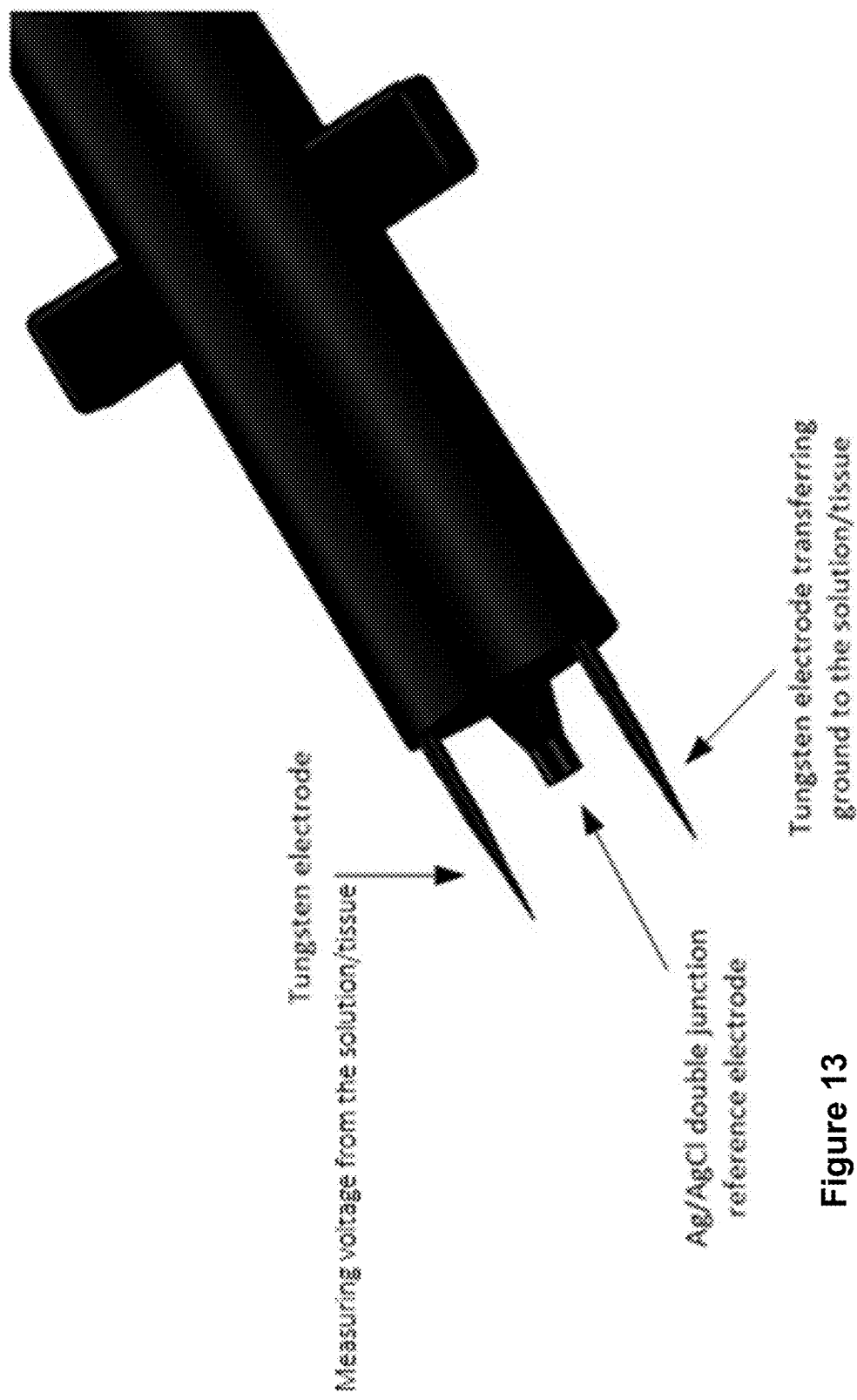
FIG. 13 is a detailed view of the electrodes that are part of a device in accordance with the invention. The first tungsten electrode measures biopotential and the second tungsten electrode transfers the printed circuit board's ground to the tissue. The third electrode is an Ag/AgCl double junction reference electrode.
Figure 14:
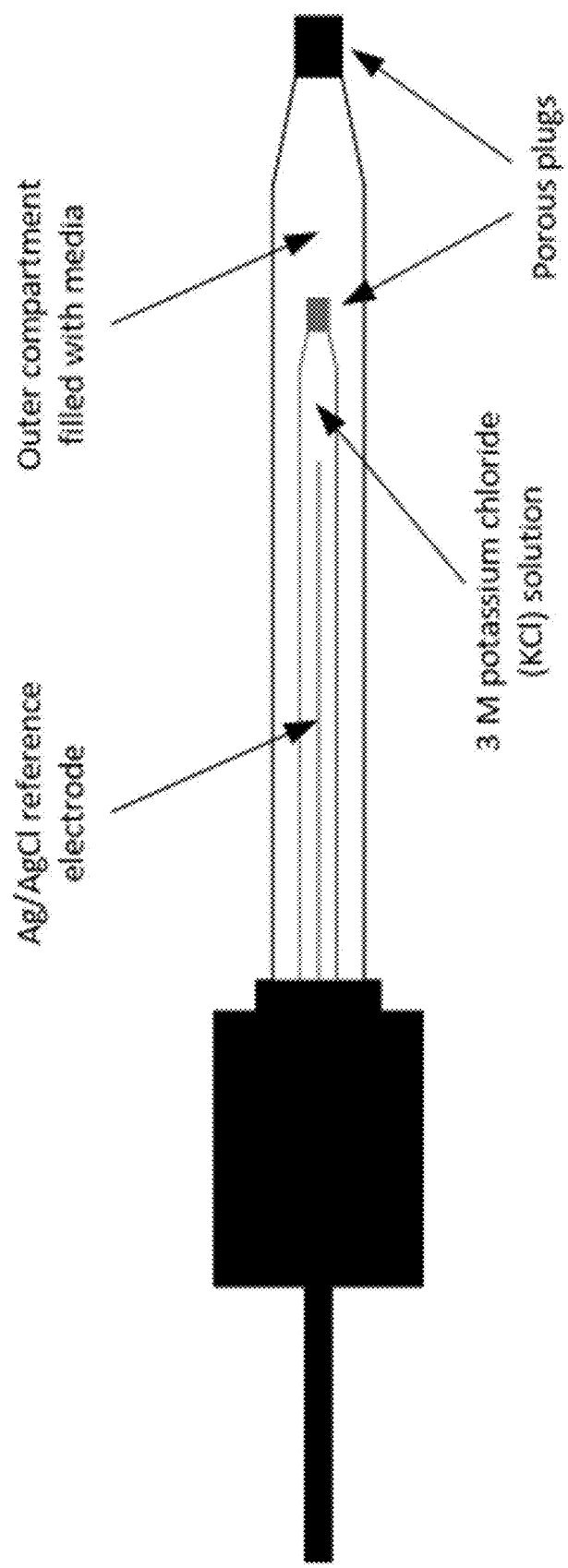
FIG. 14 is a detailed view of the Ag/AgCl double junction reference electrode that is part of a device in accordance with the invention. The double junction reference electrode is formed by inserting an Ag/AgCl reference electrode in a special chamber that contains cell culture medium.
Figure 15:
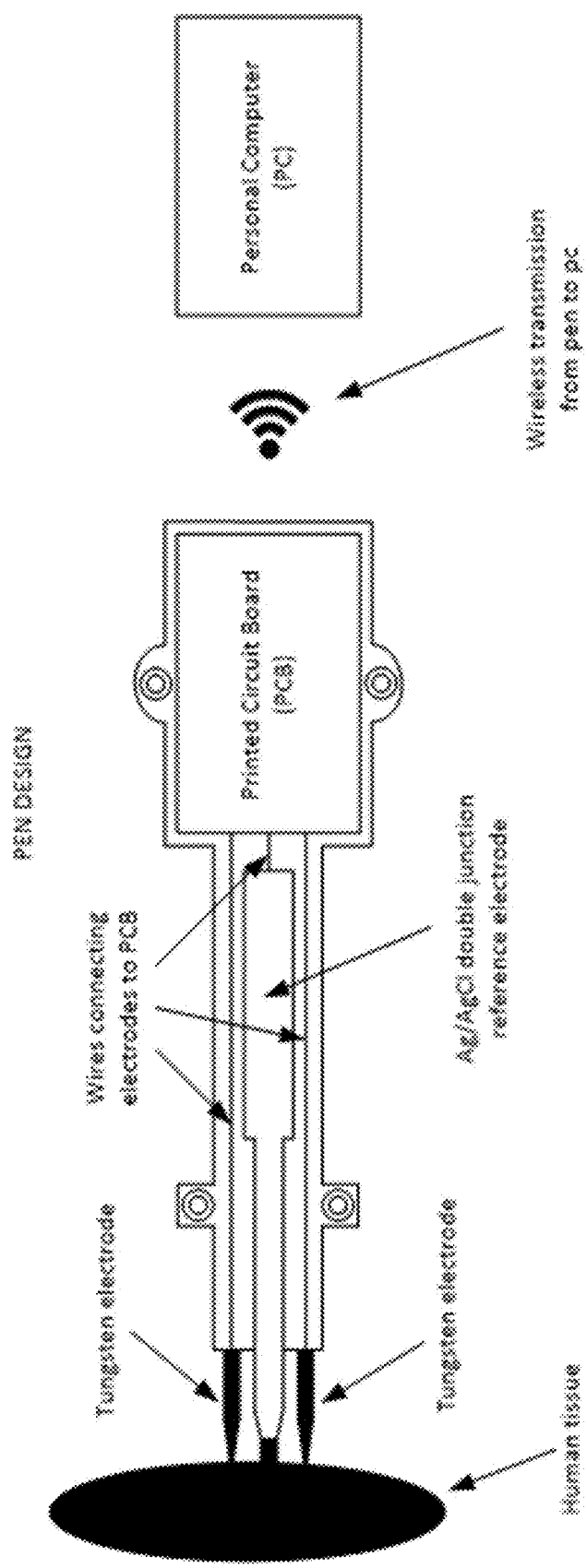
FIG. 15 is a schematic of a device in accordance with the invention, which also includes a printed circuit board (PCB) that is present in the interior of the device and a wireless connection to a computer. As can be seen from the Figure, the three electrodes that are located in the front side/tip of the device come in direct contact with the tissue when in use.
Figure 16:
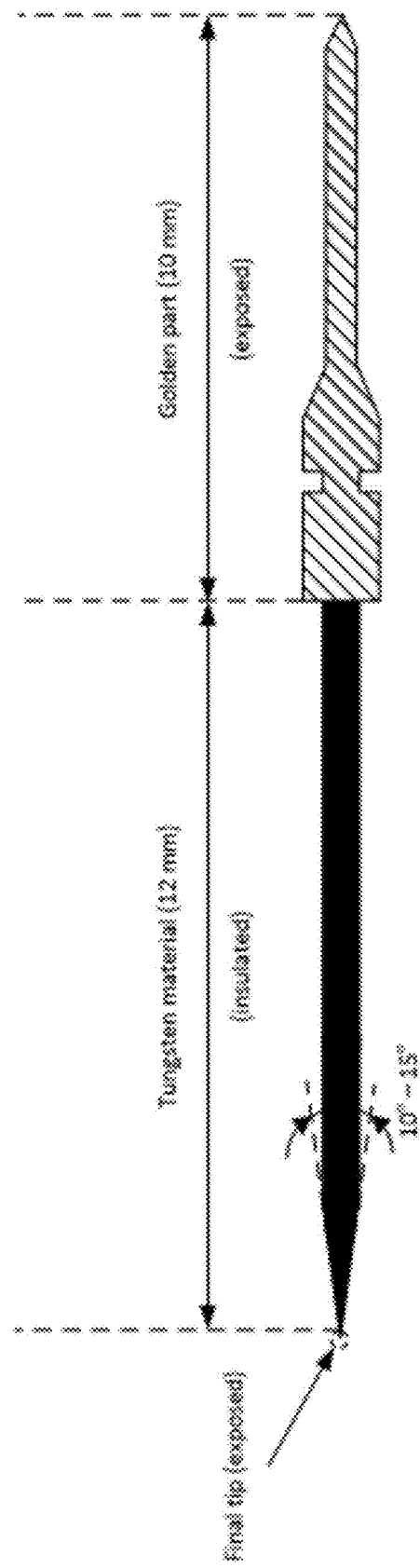
FIG. 16 is a schematic of a tungsten electrode that was part of the experimental setups used in the Examples. The impedance of a typical electrode used was measured at 1000 Hz with a maximum current of 10 nA, at a tip immersion depth of 1 mm in saline solution. The value of the electrode impedance is 3±0.6 MΩ and its metal-tip diameter is 0.3 mm.

The results for the two sets of gels are presented in FIGS. 11 and 12.

Conclusions

According to FIG. 11, if there are more ions in the material, the voltage difference between the working and the reference electrode increases. According to FIG. 12, if the material is harder (more compact), the voltage difference between the working and the reference electrode decreases. This finding is in accordance with the biopotential measurements described in Examples 1 to 3 in human tissues where cancerous tissues (which are harder structures) exhibit lower biopotential values compared to non-cancerous tissues (which are softer structures). Based on the results presented above, we conclude that this method can identify successfully voltage differences in materials which have different densities or different ion contents.

The invention claimed is:

1. A method for detecting cancerous tissue, comprising:
    contacting a sample of the tissue with a system for measuring the voltage of a tissue comprising:
        a tungsten electrode; and
        a silver/silver chloride electrode;
    detecting the voltage of the tissue sample; and
    comparing the voltage of the tissue sample to the voltage of a control sample.

2. The method according to claim 1, wherein a decreased voltage of the tissue sample compared to the control sample is indicative of cancer.

3. The method according to claim 1, wherein the tissue sample is in contact with the tungsten electrode and a medium is present that is in contact with the tissue and the silver/silver chloride electrode.

4. The method according to claim 1, wherein the tissue sample is in contact with the tungsten electrode and the silver/silver chloride electrode and a medium is present that is in contact with the silver/silver chloride electrode.

5. The method according to claim 1, wherein the silver/silver chloride electrode is a double junction reference electrode.

6. The method according to claim 1, wherein the system further comprises an instrumentation amplifier.

7. The method according to claim 1, wherein the system further comprises a medium.

8. The method according to claim 7, wherein the silver/silver chloride electrode is present within a housing, and the medium is in contact with at least the housing of the silver/silver chloride electrode.

9. The method according to claim 7, wherein the medium is also in contact with the tissue whose voltage is being measured using the system.

10. The method according to claim 9, wherein the medium is a cell culture medium.

11. The method according to claim 1, wherein one or both of the tungsten electrode and the silver/silver chloride reference electrode are held in place using a pipette tip.

12. The method according to claim 11, wherein the pipette tip has a plug.

13. The method according to claim 1, wherein the system is incorporated into a portable device.

14. The method according to claim 13, wherein the portable device further comprises a printed circuit board (PCB).

15. The method according to claim 14, wherein the portable device is connected to a data acquisition system.

* * * * *